United States Patent [19]
Hoffmann

[11] Patent Number: 5,130,236
[45] Date of Patent: Jul. 14, 1992

[54] PROCESS FOR PRODUCING DES(64,65)-PROINSULIN

[75] Inventor: James A. Hoffmann, Greenwood, Ind.

[73] Assignee: Eli Lilly and Company, Indianapolis, Ind.

[21] Appl. No.: 447,486

[22] Filed: Dec. 7, 1989

[51] Int. Cl.$^5$ .............................................. C12P 21/06
[52] U.S. Cl. ..................................... 435/68.1; 530/303
[58] Field of Search ....................... 435/68.1; 530/303

[56] References Cited

U.S. PATENT DOCUMENTS

| 3,276,961 | 10/1966 | Bodanszky et al. | 435/70.1 X |
| 4,569,792 | 6/1984 | Frank et al. | 435/68.1 |

FOREIGN PATENT DOCUMENTS

| 264250 | 4/1988 | European Pat. Off. | 435/68.1 |
| 8301074 | 3/1983 | World Int. Prop. O. | 435/68.1 |
| 8302772 | 8/1983 | World Int. Prop. O. | 435/68.1 |

OTHER PUBLICATIONS

Chevallier, Sur. J. Biochem., 5 (1968) 480–486.
Given et al., J. Clin. Invest. 76, 1398–1405 (1985).
Peavy et al., J. Biol. Chem. 260, 13989–13994 (1985).

Primary Examiner—Carolyn Elmore
Attorney, Agent, or Firm—Joseph A. Jones; Leroy Whitaker

[57] ABSTRACT

This application describes a process for producing des(64,65)-human proinsulin from human proinsulin by treating the latter with trypsin and carboxypeptidase B. The process is conducted by applying any or all of the following parameters: (1) use of an alkylated or acylated trypsin; (2) a temperature of from about 0° C. to about 10° C.; (3) a pH of from about 8 to about 10; and (4) use of a buffer selected form the group consisting of ammonium bicarbonate and glycine.

11 Claims, No Drawings

PROCESS FOR PRODUCING DES(64,65)-PROINSULIN

BACKGROUND OF THE INVENTION

U.S. Pat. No. 4,569,792 is directed to novel compounds available by conversion from human proinsulin. One of these compounds, designated des (64,65)-human proinsulin [des(64,65)HPI], has the following structure:

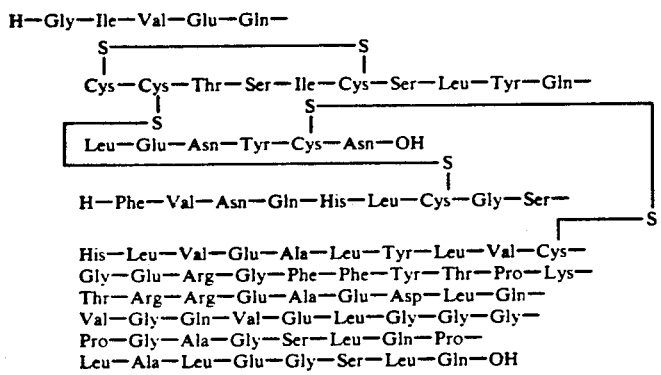

The foregoing compound differs from human proinsulin by removal of amino acids 64 and 65 with a resultant two-chain molecule joined by disulfide bonds in a manner analogous to that of human insulin.

The molecule exhibits insulin-like activity and, thus, is useful in the treatment of diabetes.

Des(64,65)HPI, as described in U.S. Pat. No. 4,569,792, was prepared in a two-step reaction sequence from human proinsulin (HPI). The human proinsulin was first treated with trypsin to produce, among others, (65-A1 split)HPI. Purified (65-A1 split)HPI treated with carboxypeptidase B yielded the desired des(64,65)HPI.

In Given et al., *J. Clin. Invest.* 76, 1398-1405 (1985), a one-step process is described for producing des(64,65)HPI from HPI. The process involves treating HPI with trypsin and carboxypeptidase B in the presence of Tris buffer at pH 7.5 at 22° C.(page 1399, column 1). This process resulted in formation of des(31,32)HPI in about a 3:1 ratio relative to des(64,65)HPI (page 1400, column 2).

A very efficient and facile method for producing des(64,65)HPI has now been discovered. This method permits a one-step conversion of human proinsulin to des(64,65)HPI in high yield. In carrying out the process of this invention, any or all of a number of parameters are employed.

SUMMARY OF THE INVENTION

In accordance with this invention, there is provided a process for producing des(64,65)-human proinsulin by digesting human proinsulin in the presence of trypsin and carboxypeptidase B, which comprises conducting the digestion under conditions which include one or more of the following:
 a) the use of an alkylated or acylated trypsin;
 b) a temperature of from about 0° C. to about 10° C.;
 c) a pH of from about 8 to about 10; and
 d) the use of a buffer selected from the group consisting of ammonium bicarbonate and glycine.

DETAILED DESCRIPTION OF THE INVENTION

The compound produced by the process of this invention has the structure as indicated in the foregoing which employs the standard three-letter shorthand designations for the amino acids. The amino acids may also be referred to by their approved single-letter designations.

These designations are as follows:

| Single-Letter | Three-Letter | Amino Acid |
|---|---|---|
| A | Ala | Alanine |
| R | Arg | Arginine |
| N | Asn | Asparagine |
| D | Asp | Aspartic Acid |
| C | Cys | Cysteine |
| E | Glu | Glutamic Acid |
| Q | Gln | Glutamine |
| G | Gly | Glycine |
| H | His | Histidine |
| I | Ile | Isoleucine |
| L | Leu | Leucine |
| K | Lys | Lysine |
| F | Phe | Phenylalanine |
| P | Pro | Proline |
| S | Ser | Serine |
| T | Thr | Threonine |
| Y | Tyr | Tyrosine |
| V | Val | Valine |

In accordance with the process of this invention, des(64,65)HPI is prepared from human proinsulin. Human proinsulin is available via a variety of routes, including organic synthesis, isolation from human pancreas by conventional methodology, and, more recently, recombinant DNA methodology.

In broad outline, the production of proinsulin using recombinant DNA methodology involves obtaining, whether by isolation, construction, or a combination of both, all of which involve now routine methods, a sequence of DNA coding for the amino acid sequence of human proinsulin. The DNA coding for human proinsulin then is inserted into a suitable cloning vehicle. The vehicle is used to transform a suitable microorganism after which the transformed microorganism is subjected to fermentation conditions leading to the production of additional copies of the human proinsulin gene-containing vector. The DNA coding for human proinsulin then is excised from the cloning vehicle and inserted in proper reading phase into an expression vehicle. The expression vehicle is used to transform a suitable microorganism after which the transformed microorganism is subjected to fermentation conditions leading to the expression of an amino acid sequence which corresponds to that human proinsulin or which contains the amino acid sequence which corresponds to that of human proinsulin.

In the event that the expression product contains the amino acid sequence of human proinsulin, it generally will comprise the human proinsulin amino acid sequence joined at its amino terminal to another peptide or protein, whether foreign or that normally expressed by the gene sequence into which the human proinsulin gene has been inserted. The human proinsulin amino acid sequence, if joined to another sequence, will be joined to such sequence through a specifically cleavable site, typically methionine. This product is customarily referred to as a fused gene product.

Assuming methionine is the cleavage site, the human proinsulin amino acid sequence is cleaved from the fused gene product using cyanogen bromide after which the cysteine sulfhydryl moieties of the human proinsulin amino acid sequence are stabilized by conversion to their corresponding S-sulfonates.

The resulting human proinsulin S-sulfonate is purified, and the purified human proinsulin S-sulfonate then is converted to human proinsulin by formation of the three properly located disulfide bonds, using, for example, the method of U.S. Pat. No. 4,430,266. The resulting human proinsulin product then is purified using recognized methodology.

As noted in the foregoing, the process of this invention involves the digestion of human proinsulin in the presence of trypsin and carboxypeptidase B. In conducting this digestion, it has been discovered that the use of certain materials and/or conditions, either applied individually or in combination, gives rise to improved results whether in terms of amount of des(64,65)HPI produced or of diminished undesired by-product. The typical undesired by-product results from cleavage of the HPI at another expected cleavage site, i..e , cleavage with removal of amino acid residues 31 and 32, leading to formation of des(31,32)HPI.

One of the parameters relates to the kind of trypsin which is used. It has been discovered that trypsin which has been pre-treated to block the ε-amino groups of its lysine residues provides superior results. Suitable blocking groups are acyl groups, alkyl groups, alkoxy groups, and the like. Thus, for example, the trypsin may be modified to acetyl trypsin, trichloroacetyl trypsin, chloroacetyl trypsin, trifluoroacetyl trypsin, formyl trypsin, carbamoyl trypsin, t-butyloxycarbonyl trypsin, carbobenzyloxy trypsin, phenylcarbamoyl trypsin, succinyl trypsin, phthaloyl trypsin, propionyl trypsin, and the like. Also, the trypsin may be alkylated at the ε-amino groups by methyl, ethyl, propyl, and the like. In addition, other agents useful in blocking the ε-amino groups of trypsin may be employed. Modified trypsins of this kind are readily prepared. Acylated trypsins, for example, are prepared by treating unmodified trypsin with the corresponding acyl anhydride. Acetylated beef trypsin is the most common and is available commercially. The latter is produced by treating beef trypsin with acetic anhydride at about ph 6.7.

The trypsin which is employed preferably is beef or pork trypsin and, when modified, preferably has been modified by acetylation. Most preferably, the trypsin is acetylated beef trypsin A second parameter found to be important in producing des(64,65)HPI from HPI is the temperature. As reported in U.S. Pat. No. 4,569,792, the typical temperature for digestion of HPI has been about room temperature or higher. It has now been discovered that the temperature of reaction is important in producing des(64,65)HPI in high yield from HPI. The temperature of reaction preferably should be from about 0° C. to about 10° C. and most preferably at the lower end of this range, that is, from about 0° C. to about 5° C.

A third parameter found to be important is the pH at which the digestion is carried out. The pH as described in U.S. Pat. No. 4,569,792 ranges from about 7 to about 7.5. It has been found, for the purpose of controlling HPI digestion with formation of des(64,65)HPI, that the pH should be higher, that is, from about 8 to about 10. The preferred pH range is from about 8.5 to about 9.5.

Although it is routine to use a buffered medium for the purpose of pH control, it has further been discovered that the identity of the buffer and not merely its ability to maintain the desired pH is also of significance in optimizing production of des(64,65)HPI. Any of a wide range of buffers are available for use in HPI digestion; however, two such buffers, ammonium bicarbonate and glycine, have been found to produce excellent control of the HPI digestion with production of the desired des(64,65)HPI. Of the two, ammonium bicarbonate is preferred.

As indicated hereinabove, this invention does not require the use of all of the foregoing parameters in combination. Only one is required. However, the use of a combination of the parameters provides optimal results relative to the use of one or more but less than all of the parameters.

Des(64,65)HPI, the compound produced by the process of this invention, exhibits an insulin-like, anti-diabetic effect substantially greater than that recognized for human proinsulin, see, for example, Peavey et al., *J. Biol. Chem.* 260, 13989–13994 (1985). Due to its insulin-like activity, des(64,65)HPI is useful in the treatment of diabetes. As such, it can be used in a variety of pharmaceutical compositions and formulations and can be administered by a variety of conventional routes, such as intramuscular, intravenous, subcutaneous, and intraperitoneal.

In administering des(64,65)HPI, the pharmaceutical forms suitable for injection include sterile aqueous solutions or dispersions and sterile powders for reconstitution into sterile injectable solutions or dispersions.

Sterile injectable solutions can be prepared by incorporating des(64,65)HPI in the calculated amount of the appropriate solvent along with various of the other ingredients, as desired.

The following examples are provided to illustrate the process of this invention. They are not intended to be limiting on the scope thereof.

EXAMPLE

Human proinsulin (5 gm; prepared in *E. coli* through recombinant DNA technology) was dissolved in 165 ml of 0.05M ammonium bicarbonate buffer at pH 9 at ambient temperature and cooled in an ice bath. Carboxypeptidase B (585 μl at 8.55 mg/ml in water) was added followed by acetylated beef trypsin (933 μl at 0.3 mg/ml in water). The resulting enzyme:substrate ratios by weight were 1:1000 for carboxypeptidase B and 1:18,000 for acetylated beef trypsin. The solution was stirred gently in an ice bath.

The reaction was stopped after 29 hrs. by adding 21 ml of 1N HCl (final pH=2.7). The entire, clear solution was pumped onto a 5.5×30 cm C-18 Vydac HPLC column. After washing with water, the protein was eluted at 8 ml/min in a 20-38% acetonitrile gradient in 0.5% trifluoroacetic acid (TFA) buffer over 32 hr. The eluant was monitored by absorbance at 276 nm, and several fractions were examined analytically by HPLC (C-8 Ultrasphere column) in an acetonitrile gradient in 0.1m sodium monobasic phosphate pH 2.2 buffer. The appropriate fractions containing intermediate-purity des(64,65)-proinsulin were pooled and lyophilized to yield 2.0 gm of material.

The material was dissolved in 200 ml of 1 m acetic acid. One-half of this solution was placed on each of two 5×200 cm G50-SF Sephadex columns equilibrated in 1 m acetic acid at 5° C. The columns were run by gravity flow in 1 m acetic acid at 5° C. Eluant fractions were collected and examined by absorbance at 276 nm and by analytical HPLC. The appropriate fractions were pooled and lyophilized to yield 1.56 gm of product, HPLC purity 98%. The structure of this product was verified to be des(64,65)-human proinsulin by amino acid composition, N-terminal sequencing analysis, fast atom bombardment (FAB) mass spectroscopy, and HPLC co-elution with an authentic standard.

The Table following presents an analysis of the results obtained using the procedure described in the foregoing Example. The conditions have been modified as the Table depicts to demonstrate the advantages of the process of this invention. These advantages are shown in terms of the amount of des(64,65)HPI formed relative to the undesired by-product, des(31,32)HPI.

TABLE

Des(64,65)HPI Formation Relative to Des(31,32)HPI via Trypsin/CPB Digest of HPI

| Trypsin | Temp., °C. | Buffer | pH | des(64,65)HPI / des(31,32)HPI |
|---|---|---|---|---|
| Beef[1] | 22 | Tris[2] | 7.5 | 0.3 |
| Pork | 5 | Tris | 8.5 | 2.2 |
| Pork | 37 | Tris | 8.5 | 0.7 |
| Pork | 2 | Tris | 6 | 1.0 |
| Pork | 2 | Tris | 6.6 | 1.8 |
| Pork | 2 | Tris | 7.6 | 2.2 |
| Pork | 2 | Tris | 8.3 | 2.7 |
| Pork | 2 | Tris | 9 | 3.1; 2.9 |
| Beef | 2 | Tris | 9 | 1.3 |
| Acetylated Beef | 2 | Tris | 9 | 4.5 |
| Pork | 5 | Tris | 10 | 2.5 |
| Pork | 5 | Amm. Bicarb. | 10 | 3.5 |
| Pork | 5 | Glycine | 10 | 3.3 |
| Pork | 5 | Phosphate | 10 | 2.4 |
| Acetylated Beef | 5 | Amm. Bicarb. | 8 | 10.8 |
| Acetylated Beef | 5 | Amm. Bicarb. | 9 | 20.8 |
| Acetylated Beef | 5 | Amm. Bicarb. | 10 | 14.3 |
| Acetylated Beef | 5 | Amm. Bicarb. | 11 | 0.1 |

[1]Given et al., J. Clin. Invest. 76, 1398-1405 (1985).
[2]Tris = Tris(hydroxymethyl)aminomethane.

I claim:

1. A process for producing des(64,65)-human proinsulin which comprises conducting the digestion of human proinsulin in the presence of acetyl trypsin, trichloracetyl trypsin, chloracetyl trypsin, trifluoroacetyl trypsin, formyl trypsin, or propionyl trypsin and carboxypeptidase B; and terminating the reaction at the optimal concentration of des(64,65)-human proinsulin.

2. Process of claim 1, in which the trypsin is acetyl trypsin.

3. Process of claim 2, in which the trypsin is acetyl beef trypsin.

4. Process of claim 1, in which the digestion is carried out at a temperature of from about 0° C. to about 10° C.

5. Process of claim 4, in which the digestion is carried out at a temperature of from about 0° C. to about 5° C.

6. Process of claim 1, in which the digestion is carried out at a pH of from about 8 to about 10.

7. Process of claim 6, in which the digestion is carried out at a pH of from about 8.5 to about 9.5.

8. Process of claim 1, in which the digestion is carried out in the presence of a buffer selected from the group consisting of ammonium bicarbonate and glycine.

9. Process of claim 8, in which the digestion is carried out in the presence of ammonium bicarbonate.

10. Process of claim 1, in which the digestion is carried out in the presence of acetyl trypsin, trichloracetyl trypsin, chloracetyl trypsin, trifluoroacetyl trypsin, formyl trypsin, or propionyl trypsin and a buffer selected from the group consisting of ammonium bicarbonate and glycine, and at a temperature of from about 0° C. to about 10° C. and a pH of from about 8 to about 10.

11. Process of claim 1, in which the digestion is carried out in the presence of acetylated beef trypsin and ammonium bicarbonate at a temperature of from about 0° C. to about 5° C. and a pH of from about 8.5 to about 9.5.

* * * * *